United States Patent [19]

Roger et al.

[11] Patent Number: 4,913,163
[45] Date of Patent: Apr. 3, 1990

[54] MEASUREMENT OF LAXITY OF ANTERIOR CRUCIATE LIGAMENT

[76] Inventors: Gregory J. Roger, 5 Kent Street, Collaroy, Australia, 2097; Mervin J. Cross, 26 Ridge Street, North Sydney, Australia, 2060

[21] Appl. No.: 153,269
[22] PCT Filed: Mar. 27, 1987
[86] PCT No.: PCT/AU87/00087
§ 371 Date: Nov. 5, 1987
§ 102(e) Date: Nov. 5, 1987
[87] PCT Pub. No.: WO87/05789
PCT Pub. Date: Oct. 8, 1987

[30] Foreign Application Priority Data

Mar. 27, 1986 [AU] Australia .............................. PH5236
Aug. 8, 1986 [AU] Australia .............................. PH7352

[51] Int. Cl.[4] .............................................. A61B 5/10
[52] U.S. Cl. ...................................... 128/782; 33/512
[58] Field of Search ....................... 128/774, 779, 782; 33/511, 512

[56] References Cited

U.S. PATENT DOCUMENTS

| T100,602 | 5/1981 | Roley et al. | 128/782 |
| 4,534,364 | 8/1985 | Lamoreux | 128/774 |
| 4,549,555 | 10/1985 | Fraser et al. | 128/728 |
| 4,583,554 | 4/1986 | Mittelman et al. | 128/774 |
| 4,583,555 | 4/1986 | Malcolm et al. | 128/782 |
| 4,799,497 | 1/1989 | Riley | 128/782 |

FOREIGN PATENT DOCUMENTS 0155857 9/1985 European Pat. Off. .
1376386 12/1974 United Kingdom .

OTHER PUBLICATIONS

Markolf et al., J. of Bone and Joint Surgery, vol. 60-A, No. 5, Jul. 1978, pp. 664-674.
Ferkel, Richard D., et al., "*Instrumented Clinical Knee Testing for Anterior-Posterior Stability: How, What, Why?*", pp. 6-20.

Primary Examiner—Francis Jaworski
Assistant Examiner—John C. Hanley
Attorney, Agent, or Firm—Fleit, Jacobson, Cohn, Price, Holman & Stern

[57] ABSTRACT

A device (10) for measurement of laxity of the knee includes a thigh support (12) and foot support (13) so arranged that the leg of the patient will be bent at the knee when the patient's thigh is resting in the thigh support (12) and his foot is strapped to the foot rest (13). A potentiometer (26) measures movement of the tibial tuberosity of the patient's leg relative to the patella, and a strain gauge mounted on plate (15) measures the force applied by a patient seeking to straighten the leg such as by tensioning the quadriceps muscle. A computer (9) plots and displays a graph (8) or other output of the force applied against the relative movement between the tibial tuberosity and the patella.

7 Claims, 4 Drawing Sheets

MEASUREMENT OF LAXITY OF ANTERIOR CRUCIATE LIGAMENT

CROSS REFERENCE TO RELATED APPLICATION(S)

This United States application stems from PCT International Application No. PCT/AU87/00087 filed Mar. 27, 1987.

TECHNICAL FIELD

The present invention relates to a device for measurement of the laxity of the anterior and/or posterior cruciate ligament of the knee of a patient and preferably also the capsular stability of the knee.

BACKGROUND ART

Damage to the anterior and/or posterior cruciate ligament and the capsule of the knee is common following trauma to the knee such as can be experienced skiing, playing football and in motor vehicle accidents to name but a few. Currently subjective interpretation of the unstable knee is made by the Orthopaedic surgeon attending the patient using a manual test such as the Lachman test. This estimation is made pre- and post-operatively and varies with the amount of force used by the surgeon in the examination. Estimating capsular laxity as opposed to cruciate ligament rupture, which has implications for the necessity of operation, is very difficult using this method.

A number of attempts have been made in the past to produce devices to objectively measure anterior and/or posterior cruciate ligament rupture. These attempts are summarized in U.S. patent specification No. 4,583,555 which itself discloses a device for this purpose. The present inventors have found that all of these prior art proposals suffer from the deficiency that they do not produce an indication of the amount of relative displacement between the femur and the tibia at a plurality of different applied forces. The present inventors provide a device which gives, in preferred embodiments, a plot of relative displacement between the femur and the tibia against an actively applied force i.e., a force applied by the patient rather than the surgeon conducting the examination.

DISCLOSURE OF THE INVENTION

The present invention consists in a device for the measurement of laxity of the knee of a patient, comprising a first support member adapted to support the thigh of a patient, a second support member adapted to support and hold the foot, ankle or lower leg of a user, the first and second support members being so placed that a leg of the patient will be bent at the knee when resting on the first and second support members, means to measure movement of the tibial tuberosity of the said leg of the patient, or of some other portion of the patient's anatomy that moves therewith, relative to the femur of the said leg of the patient, or some other portion of the patients anatomy that moves therewith, and means to measure the force applied by the patient in endeavouring to straighten the said leg such as by tensioning the quadriceps muscle.

In a preferred embodiment of the invention the movement of the tibial tuberosity is measured by the movement of a probe which contacts the tibial tuberosity and is mounted on support means which move with the femur. The most convenient way of measuring the position of the femur is in fact to measure the position of the patella which moves with the femur; other methods of detecting the relative spatial position of the femur could however be used. In a particularly preferred embodiment of the invention the support means comprises a frame pivotably connected to the device and having a bar, pad or like engagement member which rests on the patient's patella and which supports the tibial probe in contact with the tibial tuberosity. It will be realized however that the measurement of the relative movement of the tibia and of the patella could be achieved in a variety of other ways such as by using separate probes measuring independently the absolute movement of both the tibial tuberosity and the patella and integrating those measurements. In another embodiment of the invention the engagement member may rest on the tibia and the probe rest on the patella.

In a preferred embodiment of the invention the device also includes means to plot or otherwise indicate a correlation between the force applied and the relative movement between the tibial tuberosity, or some other portion of the patient's anatomy that moves therewith, and the patella produced by the application of the force.

BRIEF DESCRIPTION OF THE DRAWINGS

Hereinafter given by way of example only is a preferred embodiment of the present invention illustrated by reference to the accompanying drawings wherein.

BEST MODE OF CARRYING OUT THE INVENTION

Figure 1:
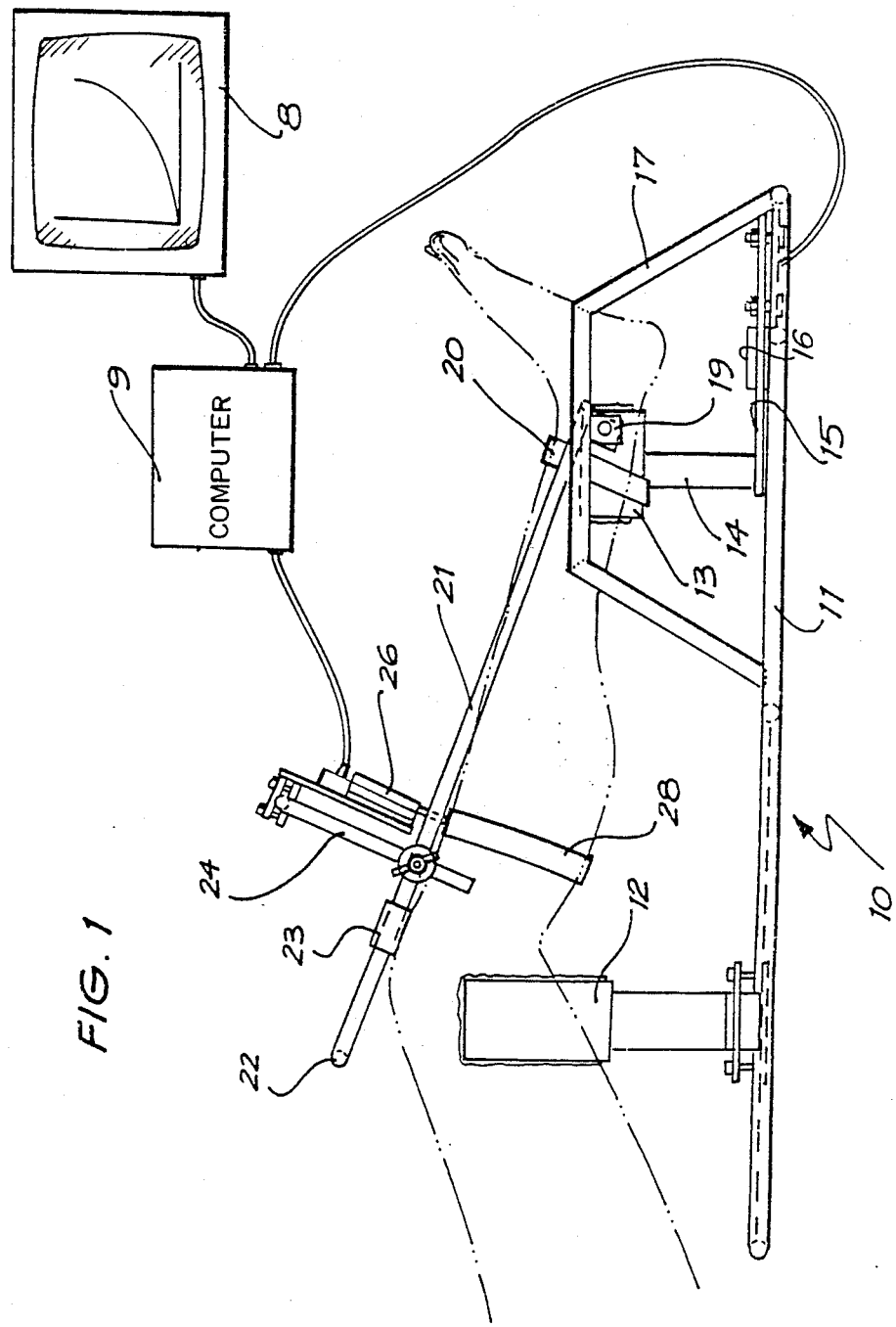
FIG. 1 is a side elevational view of a device according to the present invention with a patient positioned thereon.
Figure 2:
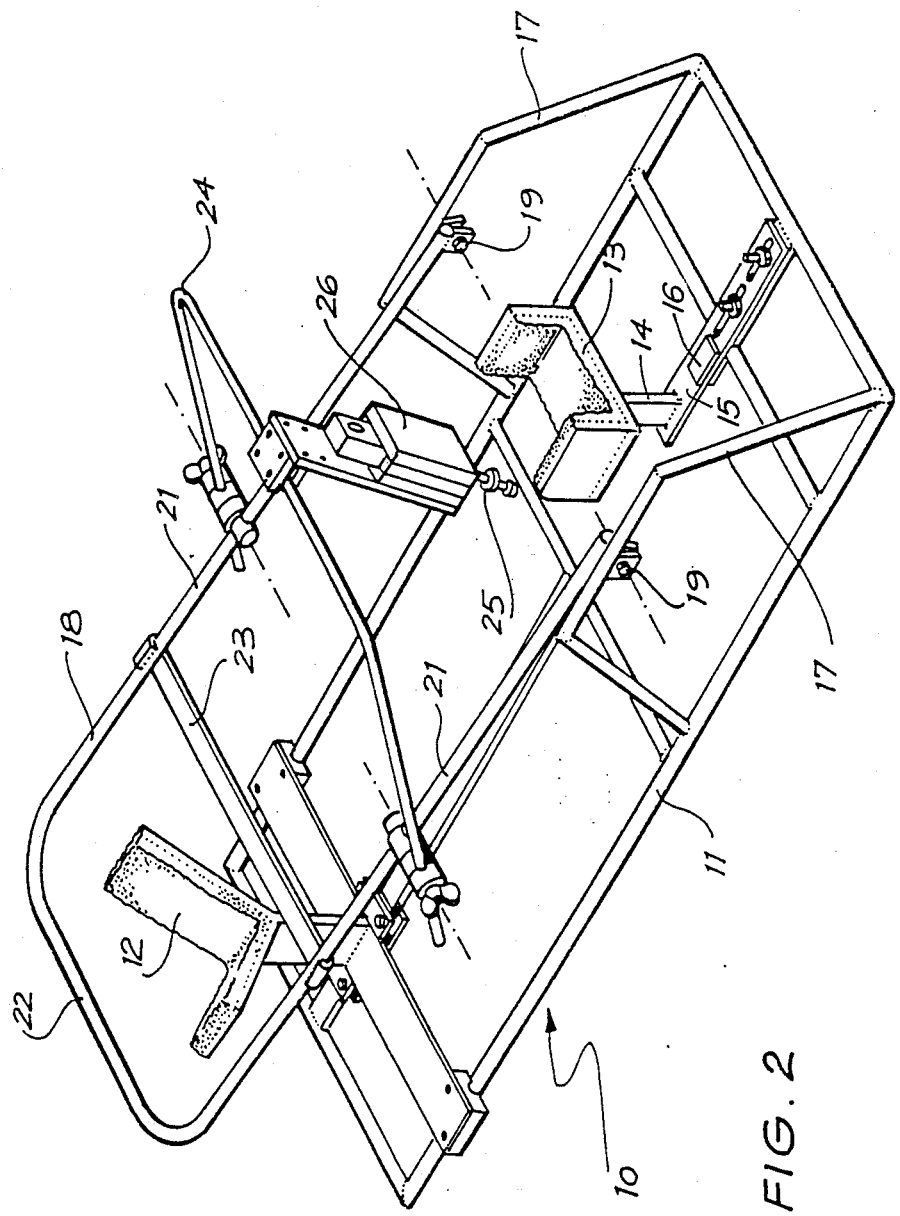
FIG. 2 is a perspective view of the device according to FIG. 1 in the absence of a patient and without showing the computer and monitor.
Figure 3:
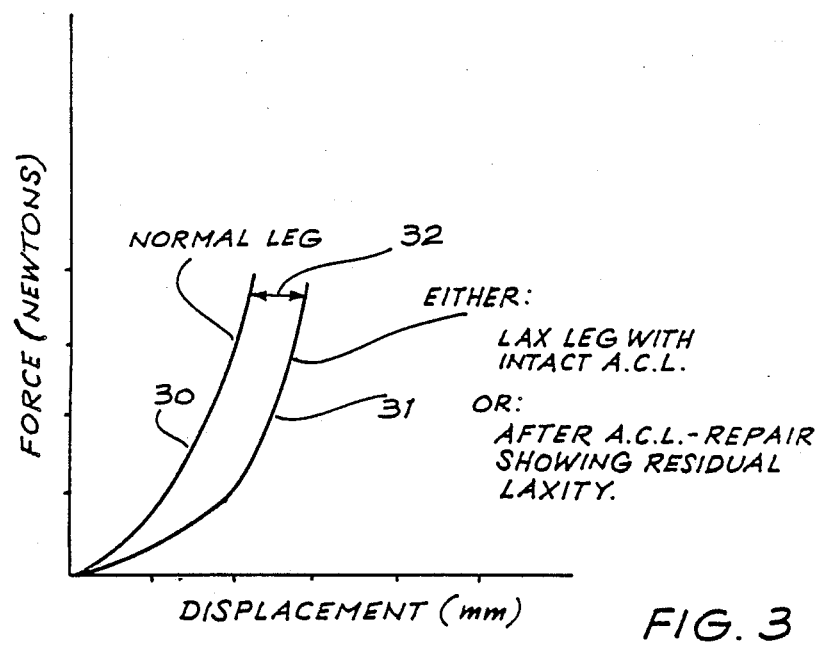
FIG. 3 is a diagrammatic representation of a typical display on the monitor of the device according to FIG. 1 showing a normal leg and a leg showing knee laxity.

The device shown in FIGS. 1 and 2 will measure objectively any physiological or abnormal, usually traumatic, laxity of the anterior cruciate ligament (ACL) of the knee to an accuracy of a fraction of a millimeter in the conscious patient. In addition capsular laxity of the knee which contributes to instability of the knee either wholly or partly can also be determined by this method and indeed discriminated from ACL rupture.

The device according to the present invention can also indicate damage to the posterior cruciate ligament even when the anterior cruciate ligament is substantially undamaged. This latter condition will show up as a considerable movement upon the initial application of force followed by a more normal incremental movement as further force is applied.

The device consists of the apparatus 10 to measure the various parameters, computing hardware 9 to process the information and a standard TV screen 8 to display the data.

The apparatus 10 comprises a base frame 11. A leg support 12 is provided at one end of the base frame 11 and is adapted to firmly support the thigh of the user. An ankle support or foot rest or foot support 13 is provided adjacent the other end of the base plate 11. The ankle support 13 comprises a horizontally extending plate 15 cantilevered from the base frame 11 and to which are connected strain gauges 16 adapted to produce a signal indicative of pressure applied to the free end of plate 15. The free end of the plate 15 carries a vertical support 14 on which the ankle support 13 is mounted. Straps 20 are provided to hold a patient's ankle firmly in contact with the ankle support 13.

A pair of upwardly extending side frames 17 are provided along side edges of base frame 11, one on either side of the ankle support 13. A U-shaped member 18 formed of a thin metal rod is pivotably connected at its free ends to a respective one of the side frames 17 by hinges 19. The member 18 has a pair of side arms 21 and a base 22. It carries a patella rest 23 extending between the side arms 21 and slideable therealong. A saddle 24 is also slideably disposed on side arms 21. The saddle 24 carries a tibial probe 25 which is connected to a potentiometer and transducer 26.

In use a patient lies on a suitable supporting surface with his thigh resting on leg support 12 and his ankle strapped to ankle support 13. The patella rest 23 is adjusted along side arms 21 until it rests on the patient's patella. The saddle 24 is also adjusted until the probe 25 rests on the tibial tuberosity of the patient. If desired the probe 25 may be held in contact with the tibial tuberosity by a strap 28 extending around the patient's leg. The patient then seeks to raise his leg by tensing his quadriceps muscle. Movement of the tibial tuberosity is measured relative to the patella by probe 25 while the force applied is measured by the strain gauges on plate 15. Signals from the transducer 26 and the strain gauges 16 can be used electronically to plot the movement against the force.

It is the task of the computing components 9 to zero the data at the commencement of the test and then to calibrate the voltage output to real units of force and distance. This is then displayed in graph form, on the TV monitor 9, along with patient details, if desired.

Interpretation of the graph allows the discrimination to be made between ACL rupture and capsular laxity. In the former case the force/displacement curve turns up quite sharply whereas in the latter case there is a smooth levelling off.

As is seen in FI. 3, as a force is applied to straighten the leg there will be an initial relative displacement of the femur and the tibia, but as further force is applied there will be less and less relative movement for a given increase in force. Line 30 shows the force/displacement graph of a normal leg while line 31 is that of a leg which is either showing capsular laxity but with an intact ACL or a leg after an ACL repair operation but showing residual laxity.

The arrow 32 indicates the amount of additional laxity in the second leg for a given applied force.

Figure 4:
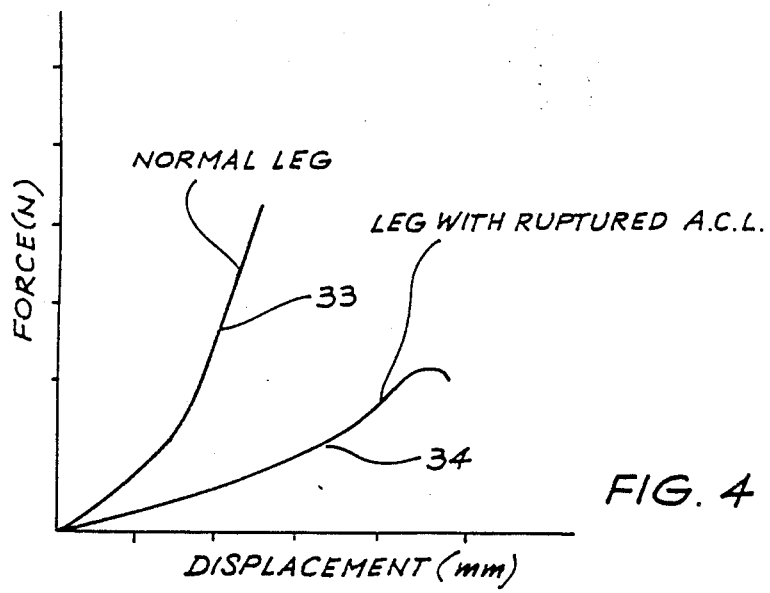
FIG. 4 is a representation similar to FIG. 3 but showing displays in respect of a normal leg and a leg showing ACL rupture.

FIG. 4 shows lines 33 and 34 which are respectively graphs of a normal leg and a leg with a ruptured cruciate ligament.

Figure 5:
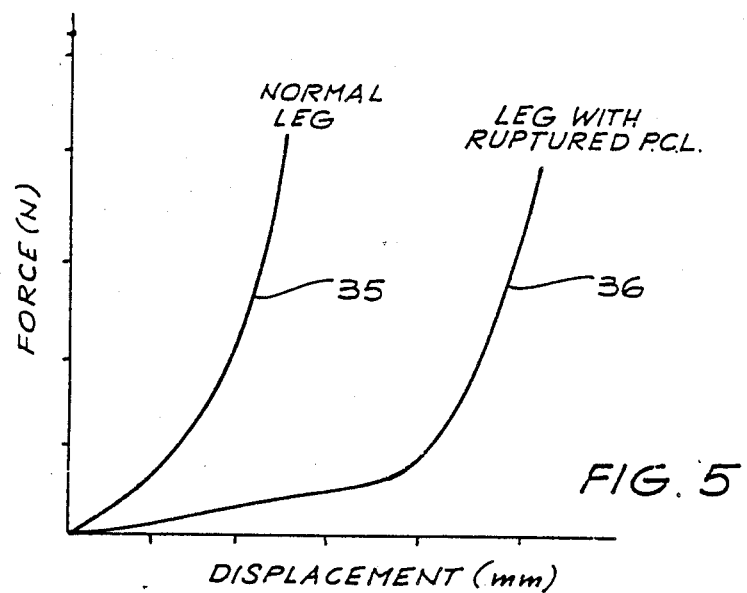
FIG. 5 is a representation similar to FIG. 3 but showing displays in respect to a normal leg and a leg with a ruptured posterior cruciate ligament.

FIG. 5 shown lines 35 and 36 which are respectively graphs of a normal leg and a leg with a ruptured posterior cruciate ligament.

Figure 6:
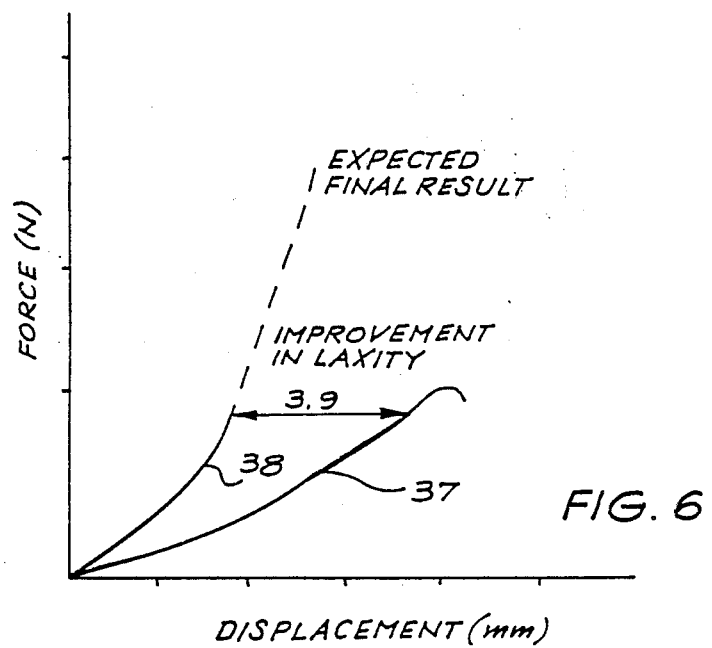
FIG. 6 is a representation similar to FIG. 3 but showing pre- and post-operation displays in respect of a leg showing ACL rupture.

FIG. 6 shows lines 37 and 38 which are respectively graphs of a pre-operative recording and a post-operative recording of a leg with ACL rupture. In the case of line 38 it can be seen that the patient is unable to apply as high a force as would be expected with a normal leg however improvement in laxity, as indicated by arrow 39, is clearly visible.

In the unconscious patient the same assessment can be made using electrical stimulation of the muscle, as opposed to voluntary effort, to demonstrate any laxity.

In an alternative embodiment of the invention the potentiometer may be positioned below the knee of the patient and connected thereto by a strap or like member such that the vertical component of any movement of the tibial tuberosity is measured as the patient endeavours to straighten his leg. The strap or like means should be such that lateral or rotational movement of the tibia is not restrained. Similarly, the potentiometer may be positioned to rest on the patella and the support bar positioned to rest on the tibial tuberosity or the tibia itself. The potentiometer will still record the relative change of position between the patella and the tibial tuberosity.

In certain circumstances it may be desirable to measure cruciate ligament laxity with the patient's leg in various positions of flexure and relative rotational juxtapositions. In the former case this can be effected by altering the position of the femoral support 12 to give the desired degree of flexure. In the latter case the rotation of the foot and the tibia relative to the femur may be achieved by having the foot rest or ankle support 13 selectively rotatably displaceable relative to plate 15. The foot rest or ankle support 13 can thus be rotated to the desired position and locked in that position. The patient's foot is then strapped to the foot rest or ankle support and the test conducted. The results so obtained may be directly compared with similar tests in other rotational positions.

We claim:

1. A device (10) for the measurement of laxity of the knee of a patient, comprising:
    a frame (11);
    first support means (12) mounted to the frame (11) for supporting the thigh of a patient;
    second support means (13) mounted to the frame (11) for supporting and holding one of the foot, ankle or lower leg of the patient, said second support means (13) being mounted to said frame (11) through a support member (14, 15) provided with at least one force transducer (16) adapted to measure the force applied by the patient to the leg supported thereon in endeavoring to straighten the leg supported thereon as by tensioning the quadriceps muscle thereof; and
    measurement means (24, 25, 26) for measuring movement of the tibial tuberosity of the said leg of the patient so supported on said first and second support means, or of a portion of the patient's anatomy which moves with said tibial tuberosity, relative to the femur of said leg or a portion of said leg which moves with said femur;
    wherein said first and second support means (12, 13) are so located relative one another on said frame as to cause the said leg of the patient so supported thereby to be bent at the knee.

2. The device according to claim 1, wherein the measurement means comprises:

a mounting means (24) arranged for moving with the patella of the patient's supported leg; and a probe (25) mounted on the mounting means and arranged for contacting the tibial tuberosity of the patient's leg or another anatomical portion of the patient's leg which moves with the tibial tuberosity, said probe moving with said tibial tuberosity or other anatomical portion as same moves relative the patella of the patient's leg.

3. The device according to claim 2, wherein the mounting means comprises:

a frame member (18) monted for pivotal movement relative the frame (11); and an engagement member (23) provided on said frame member and adapted to rest on the patient's patella; and wherein the probe is mounted to said frame member.

4. The device according to claim 1, further comprising:

means (8, 9) for indicating, as by plotting, a correlation of the measured force applied by the patient in endeavoring to straighten the supported leg with the measured relative movement between the tibial tuberosity of the patient's supported leg or another anatomical portion of the patient's supported leg which moves therewith and the femur of the patient's supported leg produced by the patient's application of force in endeavoring to straighten said leg.

5. The device according to claim 1, wherein said at least one force transducer comprises a strain gauge.

6. The device according to claim 5, wherein the second support means is adapted for supporting the foot of a patient and comprises:

a plate attached to the frame; and a foot rest mounted on said plate;

and wherein said strain gauge is mounted on said plate.

7. A method for measuring the laxity of the knee of a patient, comprising:

supporting the thigh of a leg of a patient on a first support means (12);

securing one of the foot, ankle or lower leg of said leg of said patient to a second support means (13) which is so located relative the first support means that the patient's said leg will be slightly bent at the knee when supported on said first support means and secured to said second support means, whereby the patient's said leg is caused to be slightly bent at the knee;

measuring the respective relative spatial positions of the femur and the tibial tuberosity, or of other respective portions of the patient's anatomy that move respectively therewith, of the patient's said leg;

causing the patient to endeavor to straighten said leg, as by tensioning the quadriceps muscle thereof, whereby the patient applies force to said leg;

simultaneously with the patient endeavoring to straighten said leg, measuring the force applied to said leg by the patient in endeavoring to straighten said leg;

simultaneously with the patient endeavoring to straighten said leg, measuring changes in the respective relative positions of the femur and the tibial tuberosity, or of other respective portions of the patient's anatomy that move respectively therewith, of the patient's said leg; and indicating, as by plotting, a correlation of the force applied by the patient to said leg in endeavoring to straighten said leg with the relative displacement caused thereby in the positions of the femur and the tibial tuberosity, or said other respective portions of the patient's anatomy that move respectively therewith, of the patient's said leg.

* * * * *